United States Patent [19]
Sak

[11] Patent Number: 5,549,571
[45] Date of Patent: Aug. 27, 1996

[54] BUTTERFLY ASSEMBLY WITH RETRACTABLE NEEDLE CANNULA

[76] Inventor: Robert F. Sak, 9674 Colorado Ct., Boca Raton, Fla. 33434

[21] Appl. No.: 424,942

[22] Filed: Apr. 18, 1995

[51] Int. Cl.⁶ .................................................. A61M 5/32
[52] U.S. Cl. ...................... 604/198; 604/192; 604/177; 604/110; 604/263; 128/919
[58] Field of Search ................................. 604/198, 192, 604/110, 263, 177; 128/919

[56] References Cited

U.S. PATENT DOCUMENTS

| | | |
|---|---|---|
| 4,026,287 | 5/1977 | Haller . |
| 4,804,370 | 2/1989 | Haber et al. . |
| 4,808,169 | 2/1989 | Haber et al. . |
| 4,813,936 | 3/1989 | Schroeder . |
| 4,838,870 | 6/1989 | Haber et al. . |
| 4,950,241 | 8/1990 | Ranford . |
| 4,995,870 | 2/1991 | Baskas . |
| 5,047,016 | 9/1991 | Dolgin et al. . |
| 5,108,376 | 4/1992 | Bonaldo . |
| 5,188,597 | 2/1993 | Sweeney et al. . |
| 5,221,262 | 6/1993 | Kite . |
| 5,266,072 | 11/1993 | Utterberg et al. . |
| 5,344,408 | 9/1994 | Partika . |
| 5,348,544 | 9/1994 | Sweeney et al. . |
| 5,382,235 | 1/1975 | Sak . |
| 5,382,240 | 1/1995 | Lam . |
| 5,395,347 | 3/1995 | Blecher et al. . |
| 5,498,244 | 3/1996 | Eck . |

*Primary Examiner*—Randall L. Green
*Assistant Examiner*—Perry E. Van Over
*Attorney, Agent, or Firm*—Banner & Allegretti, Ltd.

[57] ABSTRACT

A butterfly needle system provides a housing including a hollow central hub and a winged extension projecting from each side of the hub. The central hub has front and rear ends and a clip opening on an outer surface thereof. The needle cannula has a sharpened first end and extends axially through the central hub. A retaining clip is disposed on the outer surface of the central hub and extends at least partially through the clip opening. When the needle cannula is positioned in the normal extended position with the sharpened first end extending through the forward end of the hub, a lower terminal end of the retaining clip is held biased against the needle cannula. When the needle cannula is positioned in a retracted position with the sharpened first end housed within the central hub, the lower terminal end of the retaining clip is disposed in an active position adjacent the inner wall surface of the hub generally opposite to the clip opening. The needle cannula in the retracted positioned is disposed rearward of the clip opening in the central hub and the retaining clip disposed in the active position extends substantially through the vertical plane of the central hub to thereby retain the needle cannula within the central hub.

13 Claims, 4 Drawing Sheets

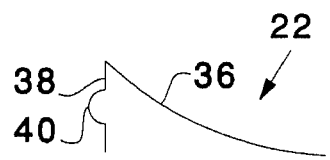
Fig. 8
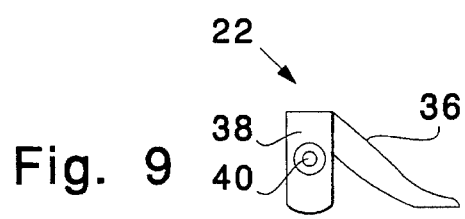
Fig. 9
Fig. 10
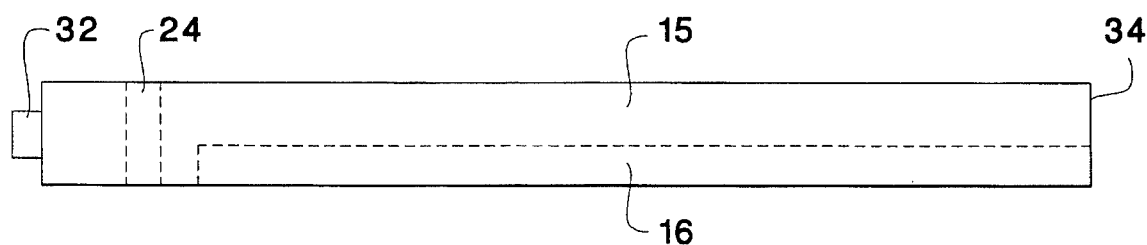
Fig. 11
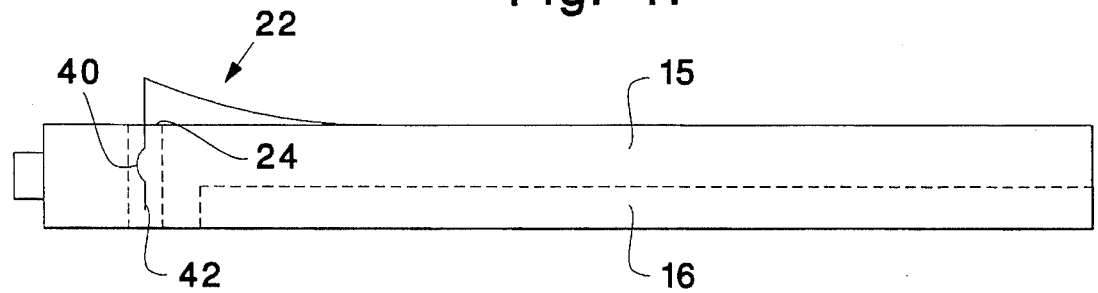

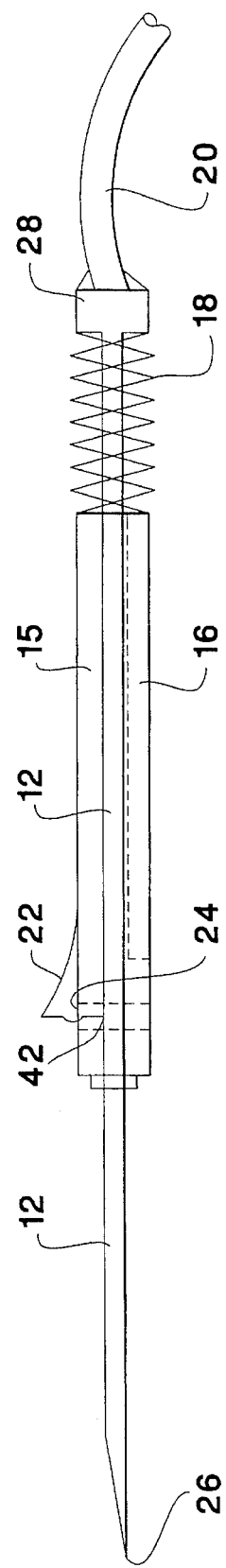
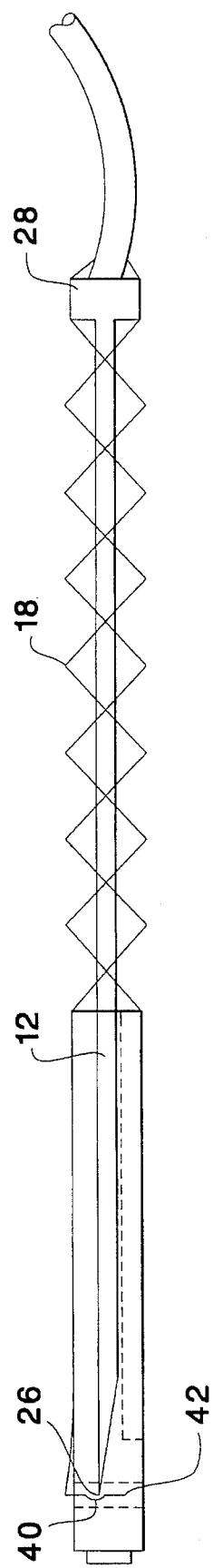

BUTTERFLY ASSEMBLY WITH RETRACTABLE NEEDLE CANNULA

TECHNICAL FIELD

The present invention relates to an intravenous butterfly needle, such as a scalp vein set or arterial venous fistula needle, and more particularly, to a butterfly needle having a needle cannula that is retractable into the winged needle housing in order to protect an operator from being inadvertently infected or injured by the used needle thereof.

BACKGROUND OF THE INVENTION

A typical prior art intravenous butterfly needle "bn", as used for the insertion into blood vessels and similar passageways in the body to permit the infusion or withdrawal of sterile fluids or blood, is illustrated in FIGS. 1 and 2. The butterfly needle generally has a hollow needle or needle cannula "n", a cylindrical hub or housing "h" for the needle, and a wing-like extension "w" extending on each side thereof. The wings of the needle assembly provide a larger surface area to which adhesive tape can be secured. This assists the technician or nurse in affixing the needle to the patient during the infusion of fluids or medicants. The wings of the needle assembly may also be folded upwards around the hub to provide a gripping extension for the technician or nurse to use when attempting to insert the needle into the desired vein, artery or other passageway.

A problem with the butterfly needles as just described is that when the sharpened end of the needle is withdrawn from the vein or artery, it remains exposed and can be a source of great danger to the operator or to anyone who might be pricked or scratched by the exposed end of the needle. Needle injuries may result in the transmission of diseases such as hepatitis and HIV and may also lead to infection. One common solution available to the operator was to simply drop the needle and its holder into a trash receptacle. Another solution is to attempt to recap the needle with a safety cover immediately after use. This, however, may in itself cause injury if the operator should accidentally stick themselves during the recapping process.

SUMMARY OF THE INVENTION

The present invention lessens the danger of being injured or infected by a used needle cannula by providing a needle cannula that is secured in its extended position for the infusion or withdrawal process and then retracted into the housing upon completion of the process.

The butterfly needle system of the present invention provides a housing including a central hub and a winged extension projecting from each side of the hub. The central hub has front and rear ends and a clip opening on an outer surface thereof. The needle cannula has a sharpened first end and extends axially through the central hub. A retaining clip is mounted on the outer surface of the central hub and extends at least partially through the clip opening. When the needle cannula is positioned in the normal extended position with the sharpened first end extending through the forward end of the hub, a lower terminal end of the retaining clip is held biased against the needle cannula. When the needle cannula is positioned in a retracted position with the sharpened first end housed within the central hub, the lower terminal end of the retaining clip is disposed in an active position adjacent the inner wall surface of the hub generally opposite to the clip opening. The needle cannula in the retracted positioned is disposed rearward of the clip opening in the central hub and the retaining clip disposed in the active position extends substantially through the vertical plane of the central hub to thereby retain the needle cannula within the central hub.

The present invention further includes the needle cannula having a flared second end extending through the rear end of the central hub and an expandable sleeve extending between the flared second end of said needle cannula and the rear end of said central hub. Thus, as the needle cannula slides axially through the central hub during movement from the extended position to the retracted position, the expandable sleeve likewise moves from a compressed state to an expanded state.

BRIEF DESCRIPTION OF THE DRAWINGS

The above description and other objects, advantages and features of the present invention will be more fully understood and appreciated by reference to the specification and accompanying drawings, wherein:

FIG. 8 is a side view of a retaining clip used in the butterfly needle system of FIG. 3;

FIG. 9 is a front view of the retaining clip shown in FIG. 8;

FIG. 10 is an enlarged side view of the housing shown in FIG. 5;

FIG. 11 is an enlarged side view of the housing shown in FIG. 5 assembled with the retaining clip shown in FIG. 8;

FIG. 12 is an enlarged side view of the butterfly needle system in accordance with the first embodiment of the present invention with the needle in an extended position; and FIG. 13 is an enlarged side view of the butterfly needle system in accordance with the first embodiment of the present invention with the needle in a retraced position within the housing.

DETAILED DESCRIPTION OF THE PREFERRED EMBODIMENTS

Figure 1:
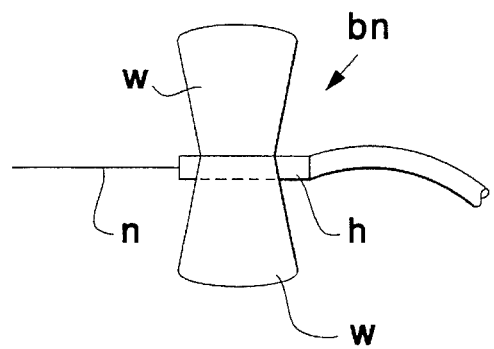
FIG. 1 is a top view of a prior art butterfly needle system.
Figure 2:
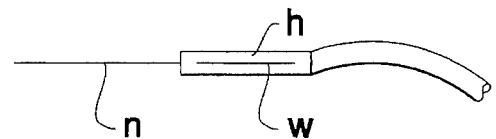
FIG. 2 is a side view of the prior art butterfly needle shown in FIG. 1.
Figure 3:
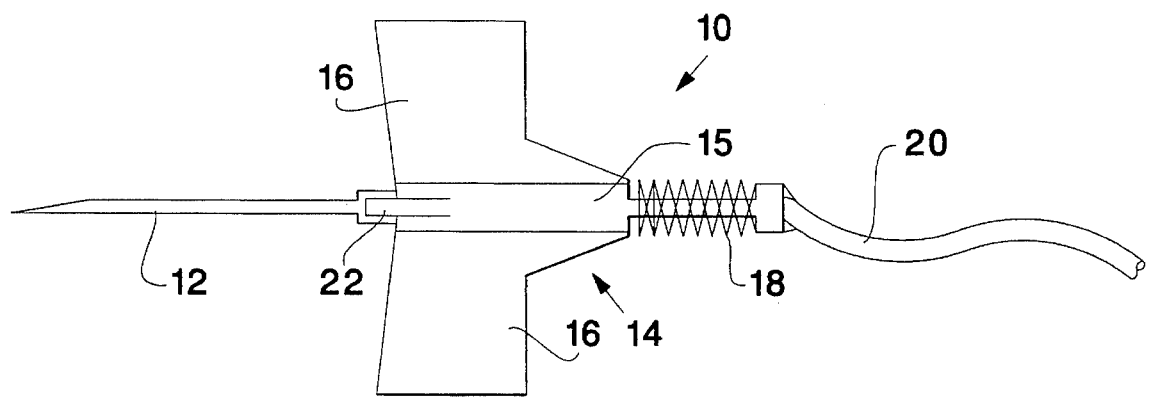
FIG. 3 is a top view of a butterfly needle system in accordance with a first embodiment of the present invention with the needle in an extended position.
Figure 4:
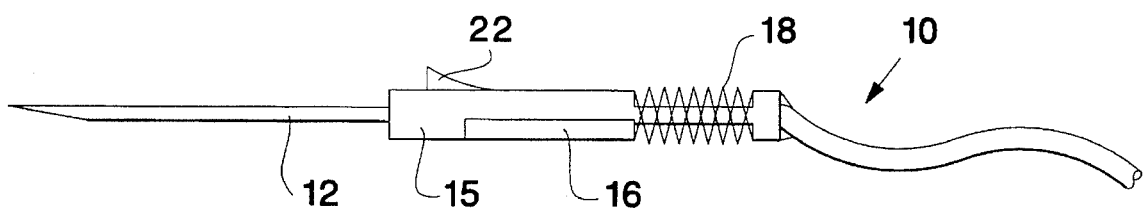
FIG. 4 is a side view of the butterfly needle system shown in FIG. 3.

Referring to FIGS. 3 and 4, a butterfly needle system 10 is generally shown in accordance with the present invention. Butterfly system 10 includes a needle cannula 12, a needle housing 14, and a wing-like extension or wing 16 extending from each side of the housing 14. System 10 further includes a flexible sleeve 18 extending between the housing 14 and tube or tubing 20 that is utilized to supply the required fluid or medicant to the needle. Butterfly needle system 10 allows for the retraction of the needle cannula into the housing after completion of the blood or fluid withdrawal/infusion process and thus reduces the risk of injury, infection or disease to the technician. For like components, butterfly needle system 10 is preferably constructed with the same materials currently in use in the prior art systems.

Figure 5:
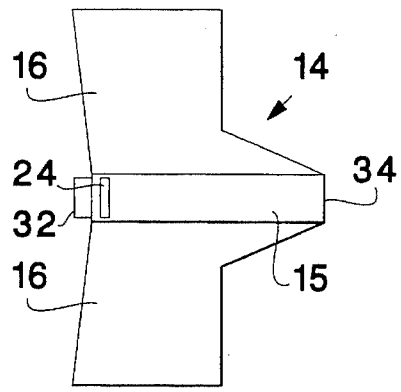
FIG. 5 is a top view of a housing used in the butterfly needle system of FIG. 3.

Referring to FIGS. 5, 10 and 11, needle housing 14 in accordance with the present invention includes a hollow central hub 15 through which needle cannula 12 extends and a wing 16 projecting from each side of hub 15. The distal end 32 of hub 15 preferably extends in front of the wings 16 in order to facilitate the needle insertion procedure. Hub 15 further includes on an upper surface thereof an opening 24 sized for the insertion of a retaining clip 22, the function of which is described below in detail. As in the prior art, wings 16 may preferably be folded upwards around central hub 15 to assist the technician with the insertion of needle cannula 12 into the vein.

Figure 6:
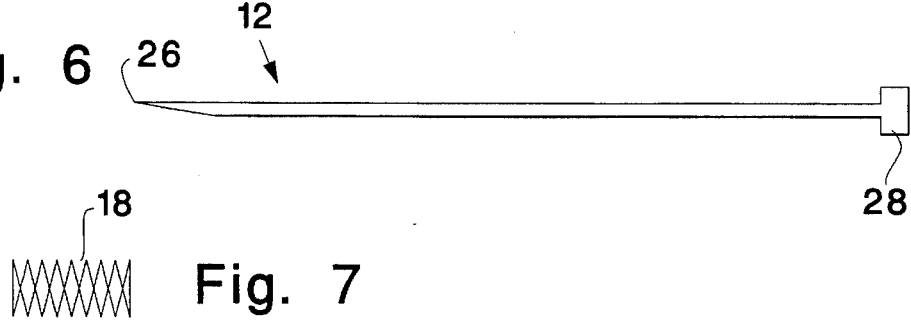
FIG. 6 is a side view of a needle cannula used in the butterfly needle system of FIG. 3.
Figure 7:
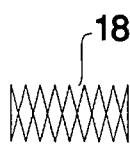
FIG. 7 is a side view of a flexible sleeve used in the butterfly needle system of FIG. 3.

Needle cannula 12 has a pointed distal end 26 and a flared proximal end 28 as shown in FIG. 6. The hollow core 30 of hub 15 has an inner diameter approximately equal to the outer diameter of needle cannula 12 such that the needle may be inserted into the hollow core 30 of hub 15 in the assembled state. As illustrated, distal end 26 of needle cannula 12 extends through the distal end 32 of the hub for ease of insertion into a patient's vein, artery or other passageway and the flared proximal end 28 extends through the proximal end 34 of the hub for attachment to supply tube or tubing 20.

The flexible accordion-like sleeve 18 is installed on the proximal end 34 of hub 15 and is also attached to the flared proximal end 28 of needle 12. When the needle 12 is in an extended position as shown in FIG. 12, flexible sleeve 18 is in a compressed state. When needle 12 is retracted within hub 15, as discussed below, the sleeve 18 expands to allow for the movement of the proximal end 28 of needle 12. In addition, a protective cover (not shown) may be installed over the distal end 26 of the needle until such time as when an operator or technician is ready to insert the needle into the patient's vein.

The retaining clip 22 illustrated in FIGS. 8 and 9 includes an axial portion 36 curving upwards and a vertical portion 38 having a convex point receptacle 40 to ensure the proper centering and retaining of the needle cannula within the housing. Retaining clip 22 is installed within the housing such that axial portion 36 rests against the outer surface of the hub and vertical portion 38 enters the hub through opening 24. Retaining clip is spring biased in the downward direction to obtain the active position within hub 15 illustrated in FIG. 11. When needle cannula 12 is in the extended position, as shown in FIG. 12, the terminal end 42 of the vertical portion 38 of retaining clip 22 enters hub 15 through opening 24 and rests against the needle cannula 12 in a passive position. Retaining clip 22 is therefore biased against needle cannula 12 such that the presence of the needle cannula actually prevents further movement of the retaining clip. Accordingly, when needle cannula 12 is in the retracted position as shown in FIG. 13, the blockage is removed and the vertical portion 38 of retaining clip 22 is repositioned in the active position generally entirely within the hub. In this active position, the terminal end 42 of the retaining clip 22 is generally adjacent to an inner hub wall surface opposite to the clip opening 24. Retaining clip 22 in the active position also extends substantially through the vertical plane of hub 15. Once retracted, the distal end 26 of needle cannula 12 is generally aligned with point receptacle 40 of retaining clip 22.

After assembly at the point of manufacture into the assembled state shown in FIG. 12, needle cannula 12 is in the extended position through the distal end of hub 32, retaining clip 22 is biased against needle cannula 12 and projects above the outer surface of hub 15 in the passive position, and flexible sleeve 18 is in the compressed state. Butterfly needle system 10 is therefore ready for use. Thus, distal end 26 of needle cannula 12 is inserted by a nurse or technician into a vein, artery or other passageway of the patient and the flared proximal end 28 of the needle 12 is connected to tubing 20 for infusion or withdrawal of the proper fluids or blood.

When the process is complete, the operator using the butterfly needle system 10 of the present invention preferably removes the needle from the patient's vein and then retracts needle cannula 12 into the central hub 15, as described below, and thereby reduces the risk of injury or transmission of disease from a used needle. The needle could also conceivably be retracted into the barrel directly from the vein, however, this procedure may tend to cause uneasiness in most patients.

Preferably, the operator applies a force in the direction of arrow "A" as shown in FIG. 13 to the flared proximal end 28 of needle cannula 12. This rearward movement of needle cannula 12 causes the pointed distal end 26 of needle cannula 12 to be retracted into hub 15. Simultaneously, when needle cannula 12 is retracted past the position of opening 24, retaining clip 22 moves downward within opening 24 and obtains the active position of FIG. 13. In addition, the rearward movement of needle cannula 12 expands flexible sleeve 18. Once retaining clip 22 moves to the active position, needle cannula 12 is safely contained within hub 15. The entire housing and needle may then be safely disposed of without risk of injury. In addition, butterfly needle system 10 prevents the needle 12 from accidently being reused. That is, there is preferably no mechanism provided for removing the retaining clip and thereafter extending needle cannula 12 through hub 15. Therefore, the operator is assured that needle cannula 12 will not be reused.

It will be obvious to one of ordinary skill in the art that numerous modifications may be made without departing from the true spirit and scope of the present invention, which is to be limited only by the appended claims.

I claim:

1. A retractable butterfly needle system comprising:

a housing including a hollow central hub and a winged extension projecting from each side of said hub, said central hub having front and rear ends and a clip opening through an outer peripheral surface thereof;

a needle cannula having a sharpened first end and extending axially through said hollow central hub;

a retaining clip disposed on said peripheral surface of said central hub and extending at least partially through said clip opening;

wherein when said needle cannula is positioned in a normal extended position with said sharpened first end extending through said forward end of said hub, a lower terminal end of said retaining clip is biased against said needle cannula; and wherein when said needle cannula is positioned in a retracted position with said sharpened first end housed within said central hub, said lower terminal end of said retaining clip is disposed in an active position adjacent an inner wall surface of said hub generally opposite to said clip opening.

2. The retractable butterfly needle system of claim 1 wherein said needle cannula includes a flared second end extending through said rear end of said central hub.

3. The retractable butterfly needle system of claim 2 further including an expandable sleeve extending between said flared second end of said needle cannula and said rear end of said central hub.

4. The retractable butterfly needle system of claim 1 wherein said needle cannula is slidable axially along said central hub for movement from said extended position to said retracted position.

5. The retractable butterfly needle system of claim 4 wherein said needle cannula in said retracted position is disposed rearward of said clip opening in said central hub.

6. The retractable butterfly needle system of claim 1 wherein said retaining clip in said active position extends through said clip opening and substantially through the vertical plane of said central hub to thereby retain said needle cannula within said central hub.

7. The retractable butterfly needle system of claim 1 wherein said retaining clip includes a convex point receptacle for aligning and centering said first end of said needle cannula in said retracted position.

8. In a butterfly needle system including a housing having a hollow central hub and a winged extension projecting from each side of said hub, a needle cannula having a sharpened first end, the needle cannula extending axially through the hollow central hub in an extended position; the improvement comprising:

a hollow central hub having a front opening, a rear opening, and an opening on an outer surface thereof;

retracting means for positioning a sharpened first end of a needle cannula in a retracted position within said hollow central hub;

retaining means for retaining said sharpened first end of said needle cannula in said retracted position, said retaining means extending through said opening on said outer surface of said central hub;

wherein a passive position said retaining means is biased against said needle cannula in said extended position; and wherein movement of said needle cannula to said retracted position thereby releases said biased retaining means to an active position such that movement of said needle cannula is thereby restricted.

9. The improvement of claim 8 wherein said needle cannula includes a flared second end, said flared second end extending through said rear opening of said central hub.

10. The improvement claim 9 further including an expandable sleeve extending between said flared second end of said needle cannula and said rear opening of said central hub.

11. The retractable butterfly needle system of claim 8 wherein said needle cannula is slidable within said central hub for movement from said extended position to said retracted position.

12. The retractable butterfly needle system of claim 11 wherein said needle cannula in said retracted positioned is disposed rearward of said opening in said outer surface of said central hub.

13. The retractable butterfly needle system of claim 8 wherein said retaining means includes a retaining clip such that in said active position said retaining clip extends through said opening in said outer surface of said central hub and substantially through a vertical plane of said central hub to thereby retain said needle cannula within said central hub.

* * * * *